United States Patent [19]

Sander et al.

[11] Patent Number: 4,998,810

[45] Date of Patent: Mar. 12, 1991

[54] ILLUMINATING DEVICE FOR AN OPERATION MICROSCOPE

[75] Inventors: Ulrich Sander, Oberkochen; Klaus Biber, Aalen, both of Fed. Rep. of Germany

[73] Assignee: Carl-Zeiss-Stiftung, Heindenheim/Brenz, Oberkochen, Fed. Rep. of Germany

[21] Appl. No.: 416,059

[22] Filed: Oct. 2, 1989

[30] Foreign Application Priority Data

Oct. 5, 1988 [DE] Fed. Rep. of Germany ....... 3833877

[51] Int. Cl.$^5$ ............................................. G02B 21/06
[52] U.S. Cl. .................................. 350/528; 350/527; 350/523
[58] Field of Search ............... 350/515, 518, 521, 523, 350/526, 527, 530, 548, 130, 449, 450, 500–502, 523–528

[56] References Cited

U.S. PATENT DOCUMENTS 3,922,699 11/1975 Yamaki .................. 350/449
4,505,555 3/1985 Piller et al. ............ 350/526
4,521,076 6/1985 Weber et al. ........... 350/449

FOREIGN PATENT DOCUMENTS 7133563 1/1987 Fed. Rep. of Germany .

Primary Examiner—Bruce Y. Arnold
Assistant Examiner—Thong Nguyen
Attorney, Agent, or Firm—Hopgood, Calimafde, Kalil, Blaustein & Judlowe

[57] ABSTRACT

An illuminating device for an operation microscope having a light source including a light guide with a light-exit surface centered on an illumination optical axis. An optical system is arranged on this axis between the light-exit surface and the main objective of the operation microscope, and the optical system comprises a converging lens, an aspheric lens and a variable-aperture diaphragm. This optical system is displaceable in the direction of its axis, and this displacement is coordinated with aperture setting of the diaphragm. The light-exit surface of the light guide is so positioned with respect to the optical system and with respect to the main objective as to illuminate the operation field with requisite size and light-distribution.

11 Claims, 2 Drawing Sheets

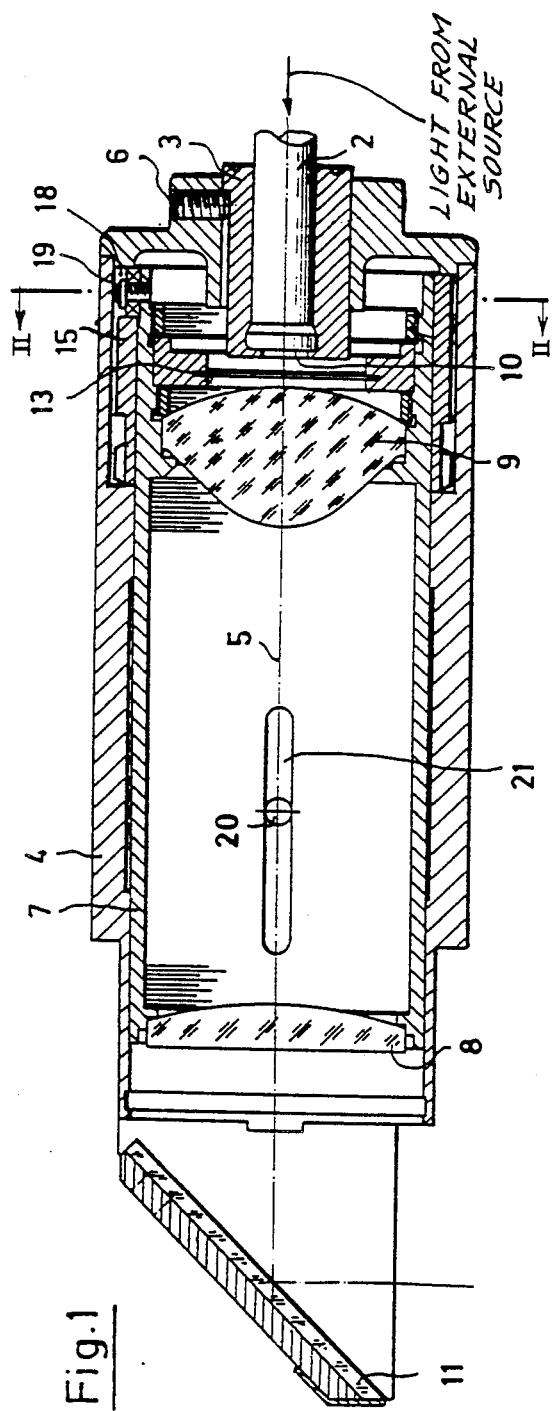
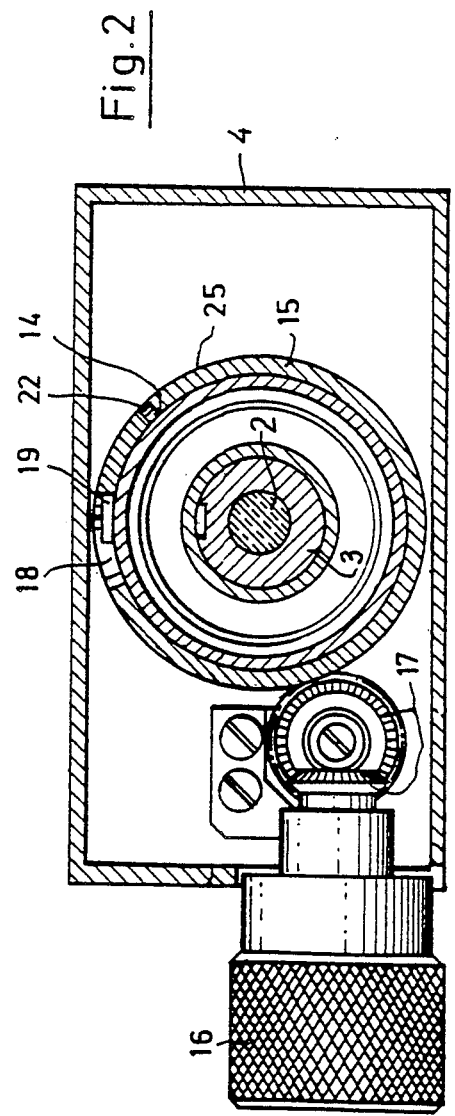

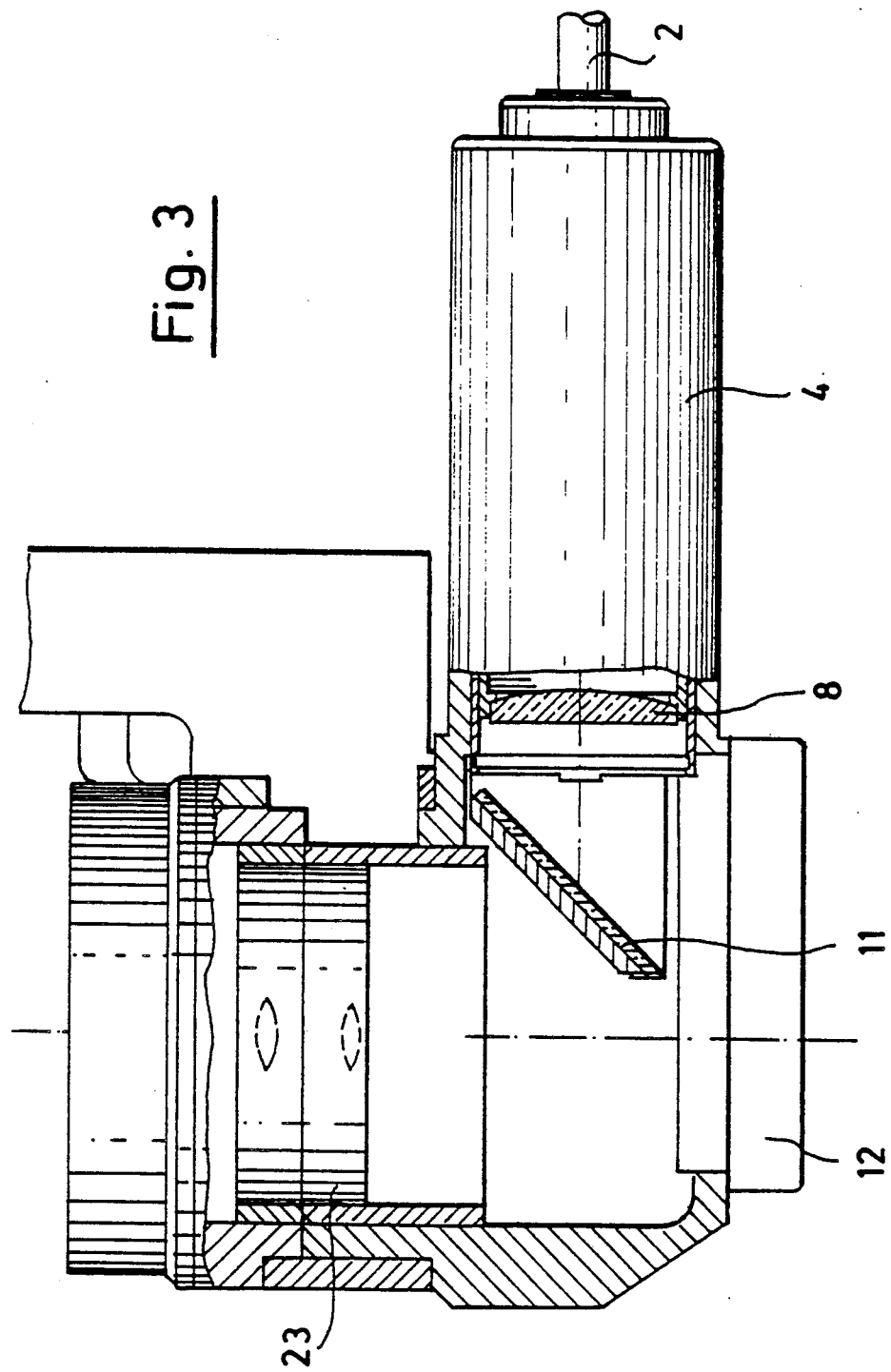

ILLUMINATING DEVICE FOR AN OPERATION MICROSCOPE

BACKGROUND OF THE INVENTION

The present invention relates to an illuminating device for an operation microscope, having a main objective for two stereoscopic observation ray paths and a source of light which includes a light guide for delivery of the light.

In operations in the fields of otorhinolaryngology, neurology and gynecology, operation microscopes must permit adjustment of both large and very small illuminated fields.

Federal Republic of Germany G 8,713,356.3 discloses an illuminating device for operation microscopes whereby it is possible to obtain different diameters of illuminated field with an invariable optical system. This known illuminating device has the disadvantage that its expansion factor does not fully satisfy the requirements specific to operations of the character indicated.

BRIEF STATEMENT OF THE INVENTION

The object of the present invention is to provide an illuminating device for an operation microscope whereby the illuminated field may have a large expansion factor which is sufficient to fully satisfy the specific requirements of such operations.

The invention meets this object by providing an optical system which is selectively and bodily displaceable along the optical axis; this optical system consists of a converging lens and an aspheric lens, as well as a diaphragm between the main objective of the operation microscope and the light-guide output (exit surface) of the illuminating device.

In one advantageous embodiment, the invention provides a linear relationship between the diameter of the diaphragm, the displacement of the optical system, and the adjusted diameter of the illuminated field; illustratively, a gear-coupled control mechanism enables such adjustment.

In another embodiment, a nonlinear correlation can be produced between the above-mentioned illumination parameters using a cam-controlled displacement mechanism. In this way, illumination can be advantageously adjusted by first partially opening the diaphragm, and then displacing the optical system in coordination with further opening of the diaphragm.

Preferably, the illuminating system is so constructed that the exit surface of the light conductor can be adjustably positioned relative to the diaphragm. Such an adjustment enables one to selectively control illumination of the object field, for homogeneity or for central emphasis, while the adjusted setting for area of the illuminated field remains the same.

The advantages attained with the invention consist, in particular, in the fact that the illuminating system is of extremely short length, gives desired illumination even in the case of large illuminated fields and, in the case of small illuminated fields, assures a good edge definition as well as a great amount of illumination, which is of particular importance in operations within narrow passages since, in such cases, light dispersion occasioned by excessively large illuminated fields impairs contrast in the working field.

DETAILED DESCRIPTION

A preferred embodiment of the invention will be described in detail, in conjunction with the accompanying drawings, in which:

FIG. 1 is a longitudinal section optical elements of an illuminating device of the invention;

FIG. 2 is a simplified right-end elevation, to show mechanical drive for optical elements of FIG. 1, partly broken-away and in section, taken at II—II of FIG. 1; and FIG. 3 is a view in elevation, partly broken-away and in longitudinal section, to show the illuminating device of FIG. 1 mounted to an operation microscope.

DESCRIPTION OF THE PREFERRED EMBODIMENT

In FIG. 1, illuminating light from an external source (not shown) enters the illuminating device via the exit surface 10 of an optical-fiber light guide 2. The exit end of light guide 2 is secured in a cylindrical housing 3 which, in turn, is arranged in the housing 4 of the illuminating device. For adjustment purposes, light guide 2 (with its housing 3) is displaceable in the direction of the optical axis 5, and a set screw 6 serves to retain a given adjustment.

Light from guide 2 exits on the axis 5 of an optical system that is carried within a tubular mount 7, which is displaceable within housing 4, in the direction of the optical axis 5. The optical system within mount 7 comprises a converging lens 8 and an aspheric lens 9. As seen in FIG. 1 and in FIG. 3 (wherein the operation microscope is seen to have a zoom or variable enlargement system 23 and a main objective 12), the illuminating optical system images the light-exit surface 10 of the light guide 2 at the viewing field of the operation microscope, via a reflecting mirror 11 and the main objective 12 of the microscope, thus passing light from the illuminating optical system through objective 12, to the exclusion of passing through the variable-enlargement system 23.

The mount 7 for the optical system 8, 9 also contains a diaphragm 13 having an aperture whose size is variable. This diaphragm can be a circular diaphragm or a slit diaphragm, or a combined circular/slit diaphragm. In FIG. 2, a lug 14 is shown for effecting a change in the aperture size of diaphragm 13, upon rotation of a cylindrical ring 15.

Within housing 4 and at the light-entrance end of mount 7, the cylindrical ring 15 is supported for rotary displacement. The rotary-adjustment knob 16 (FIG. 2) serves for effecting such displacement of ring 15, via a bevel-gear drive 17 engaging with gear-teeth 25 on the perimeter surface of ring 15, for edge-driving engagement of ring 15. Thus, by this gearing mechanism, adjusted rotation of knob 16 angularly displaces ring 15 about the optical axis 5.

Ring 15 is formed with a control groove or cam 18, which is engaged by a follower roll 19, whereby rotary adjustment of knob 16 and accompanying rotation of cam ring 15 effects displacement of the mount 7 in the direction of the optical axis, it being noted that a keying pin 20 and slot 21 engagement prevents rotation of mount 7 in housing 4.

As shown in FIG. 2, the diaphragm-setting lug 14 engages a cam groove 22 in ring 15. This engagement makes it possible for a rotary adjustment of knob 16 to additionally effect a change in the opening of diaphragm 13, in the course of rotary displacement of ring 15.

The apparatus shown and described in connection with FIGS. 1 and 2 is seen in FIG. 3 in installed relation, between the main objective 12 and the zoom or variable-enlargement system 23 of the operation microscope. Light on the delivery axis 5 from the illumination system thus passes through the main objective 12, to the exclusion of passage through the variable-enlargement system 23.

In use, the light guide 2 is first adjusted by axial shifting of its housing 3, such that illumination of the operation field is as desired. Depending upon the selectively adjusted axial distance of the light-exit surface 10 from diaphragm 13, the operation field can be either uniformly illuminated or it can be illuminated with central emphasis. Once the desired selection has been made as to the kind of field illumination, the set screw 6 should be tightened to hold the selection, for whatever subsequent adjustments may be desired via knob 16, for axial displacement of the optical system 8, 9 via mount 7, in coordination with variation in the opening of diaphragm 13.

Size of the illuminated field is controlled by actuation of knob 16. This rotates ring 15 and at the same time displaces the optical system 8, 9, together with diaphragm 13, in the direction of the optical axis. At the same time, the lug 14 and groove 22 engagement is operative to coordinate diaphragm-aperture with the indicated axial displacement.

The control cam 18 can be so profiled as to permit an initial opening of diaphragm 13, without effecting axial displacement of mount 7, the profiling being such that, upon achieving a predetermined diaphragm (13) opening, further rotation of ring 15 is operative (via cam 18) to effect the described axial displacement of mount 7, in coordination with aperture variation at diaphragm 13.

In another embodiment, the control cam 18 can be configured, from the start of knob (16) actuation, to control aperture setting and axial displacement of the optical system. And it will be understood that the control cam 18 may be designed to effect any desired program of the diaphragm-aperture setting as a function of axial displacement of mount 7, be it a linear or a nonlinear relationship.

What is claimed is:

1. An illuminating device for an operation microscope having a viewing field determined by a variable-enlargement system and a main objective, said illuminating device comprising:
   (a) a light guide having a light-exit surface on an optical axis of illumination, which axis passes through said main objective, to the exclusion of passing through said variable enlargement system;
   (b) an illuminating optical system for imaging said light-exit surface via said objective in the viewing field of the operating microscope, said optical system comprising a convergent lens and an aspheric lens in spaced relation on said axis;
   (c) a diaphragm on said axis and interposed between said optical system and said light-exit surface; and
   (d) selectively operable actuating means for displacing said optical system along said axis.

2. The illuminating device of claim 1, wherein said optical system further comprises mounting means for mounting said converging lens and said aspheric lens and said diaphragm in spaced relation, and wherein said selectively operable actuating means is operative to displace said mounting means along said axis.

3. The illuminating device of claim 1, in which said diaphragm is disposed between said aspheric lens and said light-exit surface, and in which said converging lens is disposed between said aspheric lens and said main objective.

4. The illuminating device of claim 1, in which said diaphragm has a variable aperture, and in which said actuating means is further operatively connected to said diaphragm so as to vary diaphragm aperture as a function of optical-system displacement along said axis.

5. The illuminating device of claim 4, wherein said actuating means comprises a rotatable ring having first cam means for displacement of said optical system along said optical axis of illumination as said rotatable ring is caused to rotate and second cam means for effecting variation of said diaphragm aperture as said rotatable ring is caused to rotate.

6. The illuminating device of claim 5, wherein said actuating means further comprises a rotatable knob which, when rotated, causes said rotatable ring to rotate, thereby displacing said optical system along said optical axis and varying the aperture of said diaphragm.

7. The illuminating device of claim 4, wherein the diaphragm aperture is circular and of variable diameter, and wherein said actuating means comprises a rotatable ring having first cam means for displacement of said optical system along said optical axis of illumination as said rotatable ring is caused to rotate, and second cam means for effecting diameter variation of said diaphragm aperture as said rotatable ring is caused to rotate.

8. The illuminating device of claim 7, wherein said actuating means further comprises a rotatable knob which, when rotated, causes said rotatable ring to rotate, thereby displacing said optical system in the direction of said optical axis and varying said diameter of said diaphragm aperture.

9. The illuminating device of claim 1, wherein the aperture of said diaphragm is circular and of variable diameter, and a linear relation exists between
   (a) the diameter of said diaphragm aperture,
   (b) the axial displacement of said optical system along said optical axis of illumination, and
   (c) the diameter of illuminating light imaged in the viewing field of the microscope.

10. The illuminating device of claim 1, wherein the aperture of diaphragm is circular and of variable diameter, and a non-linear relation exists between
    (a) the diameter of said diaphragm aperture,
    (b) the displacement of said optical system along said optical axis of illumination, and
    (c) the diameter of illuminating light imaged in the viewing field of the microscope.

11. The illuminating device of claim 1, further comprising mounting means for supporting said light guide near said light-exit surface, said light-guide mounting means including adjustment means for selectively displacing the position of said light-exit surface on said optical axis of illumination and with respect to said diaphragm.

* * * * *